US009123121B2

(12) United States Patent
Nishihara et al.

(10) Patent No.: US 9,123,121 B2
(45) Date of Patent: Sep. 1, 2015

(54) MAGNETIC RESONANCE IMAGING APPARATUS AND FLUID IMAGING METHOD

(75) Inventors: Takashi Nishihara, Tokyo (JP); Hiroyuki Itagaki, Tokyo (JP); Kosuke Hirai, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 111 days.

(21) Appl. No.: 13/823,837

(22) PCT Filed: Sep. 11, 2011

(86) PCT No.: PCT/JP2011/070656
§ 371 (c)(1), (2), (4) Date: Mar. 15, 2013

(87) PCT Pub. No.: WO2012/043198
PCT Pub. Date: Apr. 5, 2012

(65) Prior Publication Data

US 2013/0266199 A1 Oct. 10, 2013

(30) Foreign Application Priority Data

Sep. 27, 2010 (JP) ................................ 2010-215319

(51) Int. Cl.

| | |
|---|---|
| ***G06T 7/00*** | (2006.01) |
| ***A61B 5/055*** | (2006.01) |
| ***A61B 5/0285*** | (2006.01) |
| ***G01R 33/48*** | (2006.01) |
| ***G01R 33/563*** | (2006.01) |
| *G01R 33/483* | (2006.01) |

(52) U.S. Cl.
CPC ............ *G06T 7/0081* (2013.01); *A61B 5/0285* (2013.01); *A61B 5/055* (2013.01); *G01R 33/4818* (2013.01); *G01R 33/563* (2013.01); *G01R 33/4838* (2013.01)

(58) Field of Classification Search
None
See application file for complete search history.

(56) References Cited

U.S. PATENT DOCUMENTS

| | | | | |
|---|---|---|---|---|
| 6,549,007 | B1 * | 4/2003 | Hills et al. | 324/306 |
| 2006/0263301 | A1 * | 11/2006 | Vernon et al. | 424/9.4 |
| 2009/0212773 | A1 * | 8/2009 | Feinberg et al. | 324/309 |
| 2010/0041982 | A1 * | 2/2010 | Kitane | 600/419 |
| 2011/0031971 | A1 * | 2/2011 | Deimling et al. | 324/309 |
| 2013/0137967 | A1 * | 5/2013 | Zhang et al. | 600/413 |

OTHER PUBLICATIONS

International Search Report in PCT/JP2011/070656.

(Continued)

*Primary Examiner* — Tsung-Yin Tsai
(74) *Attorney, Agent, or Firm* — Cooper & Dunham LLP

(57) ABSTRACT

In imaging for labeling only the fluid of a specific region, a high-quality image is acquired in a short time. In order to achieve this, the optimal number of segments N is determined from the flow velocity V and the size ϕ of a specific region to be labeled when performing imaging by labeling only the fluid of the specific region using a two-dimensional selective excitation pulse as a pre-pulse. In addition, the k-space ordering is determined according to the arrival timing of the fluid to the imaging region. In addition, the optimal flip angle (FA) is determined depending on the type of pre-pulse.

11 Claims, 16 Drawing Sheets

START
S1101 ACQUISITION OF POSITIONING IMAGE
S1102 DISPLAY OF POSITIONING IMAGE
S1103 IMAGING PARAMETER DETERMINATION PROCESSING
S1104 IMAGING
S1105 IMAGE RECONSTRUCTION
END

(56) References Cited

OTHER PUBLICATIONS

N. Davies et al., "Selective Arterial Spin Labeling (SASL): Perfusion Territory Mapping of Selected Feeding Arteries Tagged Using Two-Dimensional Radiofrequency Pulses", Magnetic Resonance in Medicine, 2003, 1133-4142, 49.
S. Konstandin et al. "Selective Arterial Spin Labeling After Extra-Intracranial Bypass Surgeru", Proc. Intl. Soc. Mag. Reson. Med., 2010, 1532, 19.

* cited by examiner 100
101
102
103
104
105
106
107
108
109
110
111
112
113

(a)

(b)

605
602
(b)
414
(413)
601
603
607
604
605
D
DN
602
(a)
606
414
(413)
601

(a)

(b)

START
ACQUISITION OF POSITIONING IMAGE
S1101
DISPLAY OF POSITIONING IMAGE
S1102
IMAGING PARAMETER DETERMINATION PROCESSING
S1103
IMAGING
S1104
IMAGE RECONSTRUCTION
S1105
END

START
S1201
RECEPTION OF IMAGING PARAMETER
S1202
ACQUISITION OF FLOW VELOCITY IMAGE
S1203
DETERMINATION OF FLOW VELOCITY
S1204
CALCULATION OF THE NUMBER OF SEGMENTS N
S1205
DETERMINATION OF SEGMENT NUMBER n
S1206
DETERMINATION OF k SPACE ARRANGEMENT
END 300
321
FIRST SEGMENT
SECOND SEGMENT
N-TH SEGMENT
TReff
TI
Tpre
311
RF/
Signal
Gx
Gy
Gz
TR
310
320

START
RECEPTION OF IMAGING PARAMETER
S1301
ACQUISITION OF FLOW VELOCITY IMAGE
S130 2
DETERMINATION OF FLOW VELOCITY
S130 3
CALCULATION OF THE NUMBER OF SEGMENTS
S1304
N
DETERMINATION OF SEGMENT NUMBER n
S1305
DETERMINATION OF k SPACE ARRANGEMENT
S130 6
FA DETERMINATION
S1307
END

Dscope
800
602
414
801
603

MAGNETIC RESONANCE IMAGING APPARATUS AND FLUID IMAGING METHOD

TECHNICAL FIELD

The present invention relates to a magnetic resonance imaging (hereinafter, referred to as MRI) technique. In particular, the present invention relates to an imaging parameter determination technique in imaging combined with a pre-pulse that is applied ahead of actual imaging.

BACKGROUND ART

In MRI imaging, a pre-pulse may be applied to selectively excite a proton signal of a specific region, thereby improving the image quality or imaging the additional information. When selectively exciting only a proton signal of a specific region, an RF pulse for two-dimensional selective excitation and a gradient magnetic field for two-dimensional selective excitation are applied in combination. Examples of such an RF pulse for two-dimensional selective excitation (two-dimensional selective excitation pulse) include a labeling IR (Inversion Recovery) pulse in ASL (Arterial Spin Labeling) which gives a magnetic mark (label) to the blood flow.

Since the IR pulse is often applied to the fluid outside the imaging plane, the timing at which the fluid flows into the imaging plane after IR pulse is applied has a large influence on image quality. When the IR pulse is used as a two-dimensional selective excitation pulse, the labeling range is narrower than that in the normal case. For this reason, the case where the IR pulse is used as a two-dimensional selective excitation pulse is more sensitive to timing.

As a specific example of application, there is non-contrast perfusion (refer to NPL 1) or renal artery imaging (refer to NPL 2).

CITATION LIST

Non-Patent Literature

[NPL 1] Selective Arterial Spin Labeling (SASL): Perfusion Territory Mapping of Selected Feeding Arteries Tagged Using Two-Dimensional Radiofrequency Pulses, Nigel P. Davies and Peter Jezzard, Magnetic Resonance in Medicine 49:1133-1142 (2003)

[NPL 2] Renal Arteries: Navigator-gated Balanced Fast Field-Echo Projection MR Angiography with Aortic Spin Labeling: Initial Experience, Elmar Spuentrup, MD, Warren J. Manning, MD, Peter Boernert, PhD, Kraig V. Kissinger, RT, MS Rene'M. Botnar, PhD, Matthias Stuber, PhD, Radiology: Volume 225: 589-596 (2002)

SUMMARY OF INVENTION

Technical Problem

The MRI apparatus repeats measurement to collect echo signals for one phase encoding by applying a high-frequency magnetic field, thereby filling k space. In this case, there is a method called segment measurement to shorten the imaging time by measuring echo signals of a plurality of segments after one application of a pre-pulse instead of dividing k space into a plurality of regions (segments) and applying the pre-pulse to each segment. When labeling the fluid of a specific region using a two-dimensional selective excitation pulse as a pre-pulse, the labeling becomes insufficient if the number of segments N, the diameter (size) $\phi$ of the excitation region of the two-dimensional selective excitation, and the flow velocity V of the fluid to be imaged, which are measured after one application of the pre-pulse, are not appropriately set.

For example, assuming that the number of segments N and the size $\phi$ are fixed, the number of times by which the two-dimensional selective excitation pulse is applied while the fluid passes through the excitation region (size $\phi$) decreases as the flow velocity V increases. Therefore, if the number of segments N to be set is too large, labeling becomes insufficient when the flow velocity V is high. As a result, a contrast reduction or artifacts occur. On the other hand, if the number of segments is too small, it is not possible to reduce the imaging time.

The present invention has been made in view of the above-described situation, and it is an object of the present invention to provide a technique of acquiring a high-quality image in a short time in imaging for labeling only the fluid of a specific region.

Solution to Problem

The present invention determines the optimal number of segments N from the flow velocity V and the size 0 of a specific region to be labeled when performing imaging by labeling only the fluid of the specific region using a two-dimensional selective excitation pulse as a pre-pulse. In addition, the k-space ordering is determined according to the arrival timing of the fluid to the imaging region. In addition, the optimal flip angle (FA) is determined depending on the type of pre-pulse.

Specifically, there is provided a magnetic resonance imaging apparatus that acquires an image of a fluid by applying a two-dimensional selective excitation pulse as a pre-pulse and measuring echo signals of one or more segments each time the two-dimensional selective excitation pulse is applied. The magnetic resonance imaging apparatus includes: imaging parameter determination means for determining the number of segment execution times, which is the number of segments measured each time the two-dimensional selective excitation pulse is applied, from a velocity of a fluid to be imaged, a size of an excitation region of the input two-dimensional selective excitation pulse, and measurement time per segment.

In addition, there is provided a fluid imaging method using a magnetic resonance imaging apparatus that acquires an image of a fluid by applying a two-dimensional selective excitation pulse as a pre-pulse and measuring echo signals of one or more segments each time the two-dimensional selective excitation pulse is applied. The fluid imaging method includes: an imaging parameter determination step of determining the number of segment execution times, which is the number of segments measured each time the two-dimensional selective excitation pulse is applied, from a velocity of a fluid to be imaged, a size of an excitation region of the input two-dimensional selective excitation pulse, and measurement time per segment; a measurement step of measuring echo signals of each segment by the number of segment execution times and arranging the acquired echo signals in k space each time the two-dimensional selective excitation pulse is applied; and an image reconstruction step of reconstructing an image from the echo signals arranged in k space.

Advantageous Effects of Invention

According to the present invention, a high-quality image can be acquired in a short time in imaging for labeling only the fluid of a specific region.

DESCRIPTION OF EMBODIMENTS

<<First Embodiment>>

Figure 1:
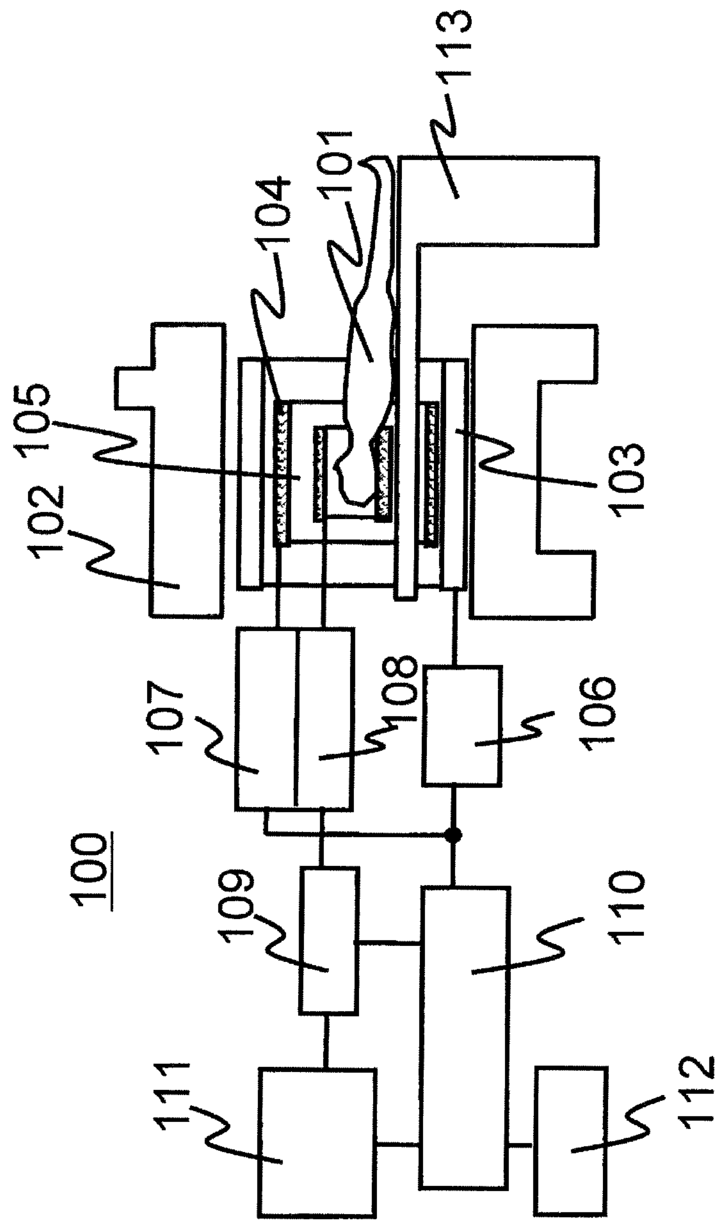
FIG. 1 is a block diagram of an MRI apparatus of a first embodiment.

Hereinafter, a first embodiment to which the present invention is applied will be described. Hereinafter, in all drawings for explaining the embodiments of the present invention, the same reference numerals are given to elements having the same functions, and repeated explanation thereof will be omitted.

First, the configuration of an MRI apparatus of the present embodiment will be described. FIG. 1 is a functional block diagram of an MRI apparatus 100 of the present embodiment. The MRI apparatus 100 of the present embodiment includes a magnet 102, a gradient magnetic field coil 103, a high-frequency magnetic field (RF) coil 104, an RF probe 105, a gradient magnetic field power source 106, an RF transmission unit 107, a signal detection unit 108, a signal processing unit 109, a control unit 110, a display unit 111, an operating unit 112, and a bed 113.

The magnet 102 generates a static magnetic field in a region (examination space) around an object 101. The gradient magnetic field coil 103 is formed by coils in three directions of X, Y, and Z, and generates a gradient magnetic field in the examination space according to a signal from the gradient magnetic field power source 106. The RF coil 104 applies (emits) an RF to the examination space according to the signal from the RF transmission unit 107. The RF probe 105 detects an MR signal generated by the object 101. The signal received by the RF probe 105 is detected by the signal detection unit 108, is subjected to signal processing by the signal processing unit 109, and is input to the control unit 110.

The control unit 110 reconstructs an image from the input signal and displays it on the display unit 111. In addition, the control unit 110 controls the operations of the gradient magnetic field power source 106, the RF transmission unit 107, and the signal detection unit 108 according to the time chart of control stored in advance and the imaging parameters input by the operator through the operating unit 112. In addition, the time chart of control is generally called a pulse sequence. The timings of the above-described irradiation of the high-frequency magnetic field, application of the gradient magnetic field, and detection of an echo signal are specified in the pulse sequence.

The control unit 110 includes a CPU, a memory, and a storage device, and various kinds of processing are realized when the CPU loads a program stored in the storage device to the memory and executes it.

In addition, the bed 113 is intended for the object lying. In addition, the MRI apparatus 100 may further include a shim coil for correcting the non-uniformity of the static magnetic field in the examination space and a shim power source for supplying a current to the shim coil.

An imaging target of the current MRI is a proton which is a main component of the object 101. The shapes or functions of the head, abdomen, limbs, and the like of the human body are imaged in a two-dimensional or three-dimensional manner by imaging the spatial distribution of proton density or the spatial distribution of relaxation of the excited proton.

Figure 2:
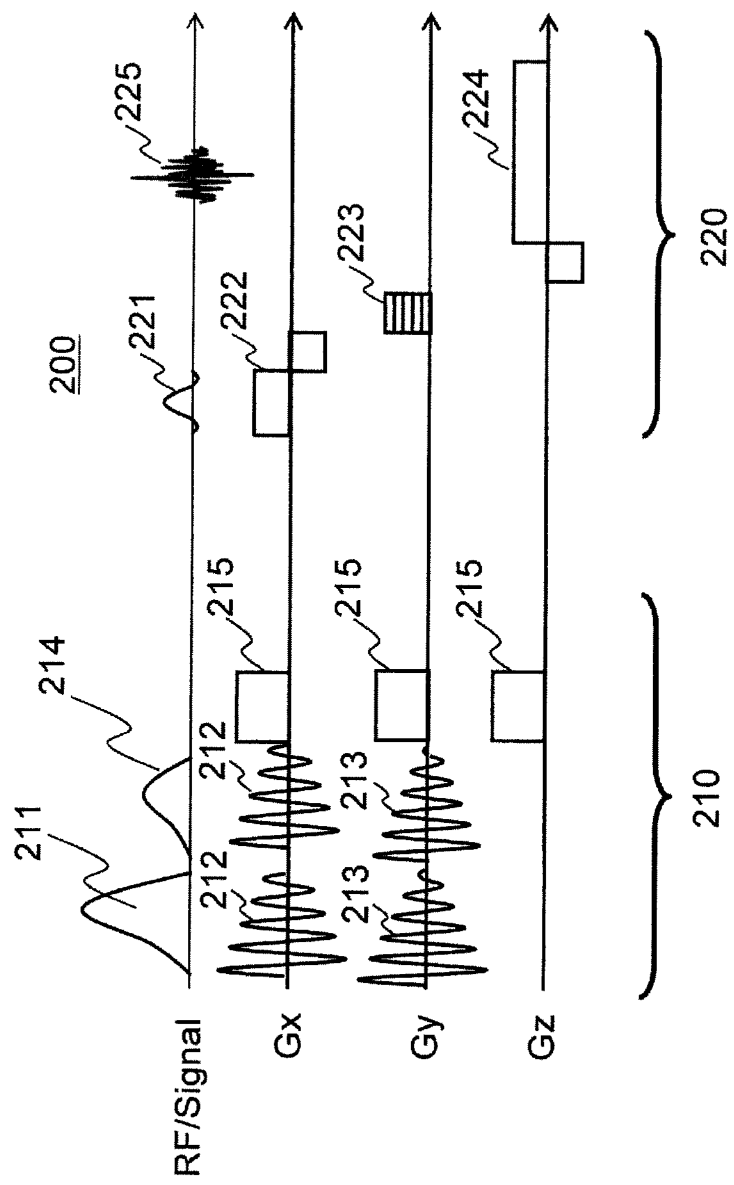
FIG. 2 is an explanatory diagram illustrating the pulse sequence to apply the two-dimensional selective excitation pulse as a pre-pulse.

In the present embodiment, imaging is performed by applying a combination of an RF pulse for two-dimensional selective excitation and a gradient magnetic field for two-dimensional selective excitation as a two-dimensional selective excitation pulse and performing labeling only in the fluid of a specific region. In this case, a plurality of echo signals are acquired after one application of pre-pulse. Prior to explaining the pulse sequence of the present embodiment, an example of a typical pulse sequence 200 which acquires an echo signal once after applying a two-dimensional selective excitation pulse using the two-dimensional selective excitation pulse as a pre-pulse will be described with reference to FIG. 2. In this drawing, RF/Signal, Gx, Gy, and Gz indicate axes of RF pulse and echo signal, a gradient magnetic field in an X-axis direction, a gradient magnetic field in a Y-axis direction, and a gradient magnetic field in a Z-axis direction, respectively. In addition, these are the same in each pulse sequence diagram of this specification.

The pulse sequence 200 includes a pre-pulse portion 210 and actual imaging portion 220. The pre-pulse portion 210 is executed in advance of the actual imaging portion 220, and applies a two-dimensional selective excitation pulse to give a label to the fluid of a specific region, for example. As described above, the two-dimensional selective excitation pulse is for selectively exciting a region restricted in an arbitrary two-dimensional direction, and includes an RF pulse (RF pulse for two-dimensional selective excitation) 211 (214) and two orthogonal gradient magnetic fields (gradient magnetic fields for two-dimensional selective excitation) 212 and 213 which change (vibrate) over time. The RF pulse for two-dimensional selective excitation and the gradient magnetic field for two-dimensional selective excitation are simultaneously applied.

Examples of the RF pulse for two-dimensional selective excitation which is applied include an IR pulse 211 for inverting the fluid and a pre-saturation pulse 214 for eliminating the fluid.

The pre-saturation pulse 214 is applied together with a gradient magnetic field 215.

In the actual imaging portion 220, an RF pulse for two-dimensional selective excitation 221 and a gradient magnetic field (slice selection gradient magnetic field) 222 for selecting a slice are first applied. In this case, a phase encoding gradient magnetic field 223 is applied to give different phase encoding to echo signals 225. As the number of phase encoding to be given, the value of 128, 256, 512, or the like per image is usually selected.

Each echo signal 225 is collected as a time-series signal, which usually includes 128, 256, 512, or 1024 sampling data items, while applying a reading encoding gradient magnetic field 224. In addition, the control unit 110 performs a Fourier transform (hereinafter, referred to as FT) of these data items to generate an MR image.

In the present embodiment, k space is divided into a plurality of regions (segments) and a two-dimensional selective excitation pulse is applied once, and then segment measurement for measuring echo signals of the plurality of segments is performed. Hereinafter, the measurement of an echo signal of one segment may be simply written as a segment. In each segment, echo signals of one phase encoding are collected after one application of the RF pulse for two-dimensional selective excitation 221. In addition, in the case of three-dimensional imaging, echo signals of one phase encoding (that is, one point of (ky·kz) space) of one slice encoding are collected.

Figure 3:
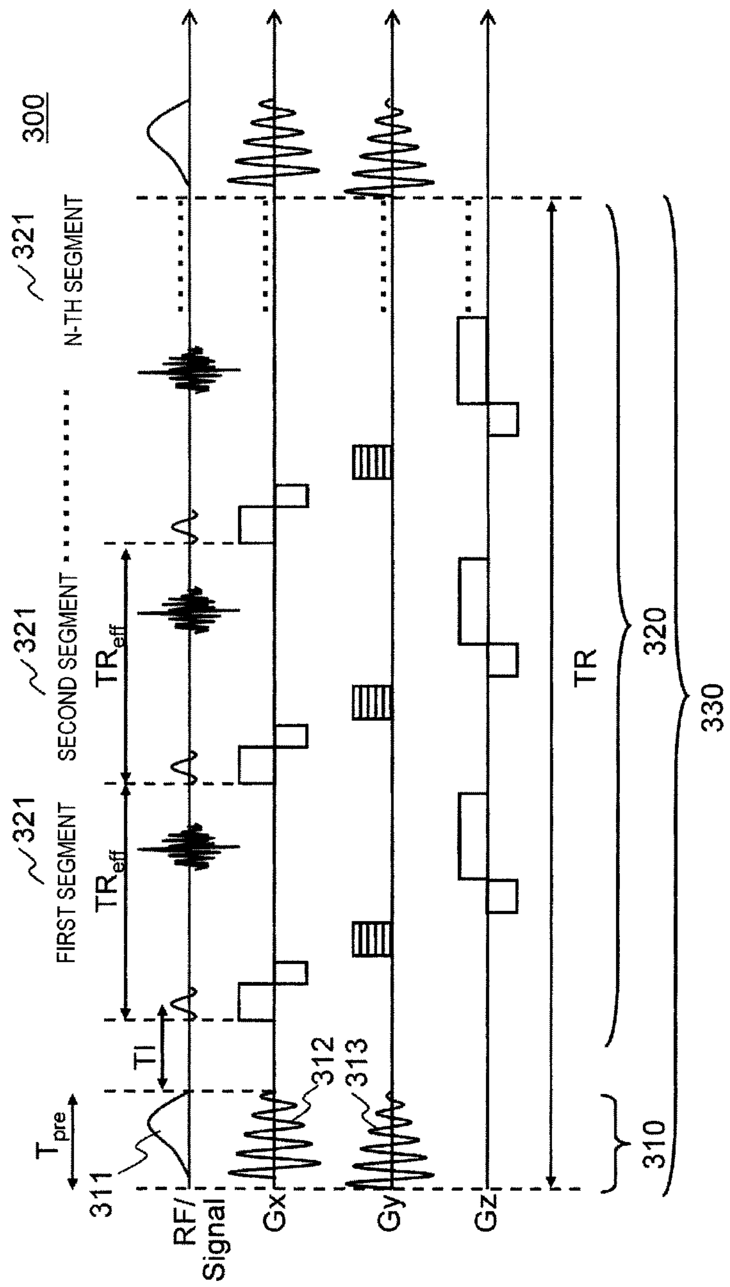
FIG. 3 is an explanatory diagram illustrating the pulse sequence of the first embodiment.

FIG. 3 shows a pulse sequence 300 of the present embodiment. In a pre-pulse portion 310, an RF pulse for two-dimensional selective excitation 311 is applied together with gradient magnetic fields for two-dimensional selective excitation 312 and 313. Then, in actual imaging portion 320, a segment 321 is executed N times. Within each segment 321, the same pulse sequence as the above-described actual imaging 220 is executed. In the present embodiment, necessary echo signals are collected by repeating a phase 330 including the pre-pulse portion 310 and the actual imaging portion 320. In addition, in the final phase 330, a segment 321 does not necessarily need to be executed N times.

The application time of two-dimensional selective excitation pulses (RF pulse for two-dimensional selective excitation 311 and gradient magnetic fields for two-dimensional selective excitation 312 and 313) is set to $T_{pre}$, the measurement time of each segment 321 is set to $TR_{eff}$, the application interval (repetition interval of the phase 330) of the RF pulse for two-dimensional selective excitation 311 is set to repetition time TR, and time from the application of the RF pulse for two-dimensional selective excitation 311 to the start of actual imaging is set to waiting time TI. In addition, the segments 321 executed after the application of the pre-pulse 311 are called a first segment, a second segment, . . . , and an N-th segment in order of execution.

When performing segment measurement by labeling only the fluid of a specific region by applying a two-dimensional selective excitation pulse as a pre-pulse as described above, the number of segments N which optimizes the labeling and total imaging time is determined by the flow velocity V and the size ϕ of a region excited by the two-dimensional selective excitation pulse.

The control unit 110 of the present embodiment includes a parameter determination section 500 that determines parameters required for the execution of the pulse sequence, such as the number of segments N and the k-space ordering, from imaging parameters input by the operator. The parameter determination section 500 performs parameter determination processing to determine the number of segments N and the k-space ordering.

The control unit 110 executes imaging according to the pulse sequence set in advance so that the k-space ordering determined by the parameter determination section 500 is realized, using the input imaging parameters and the number of segments N determined by the parameter determination section 500. Then, an image is reconstructed from the obtained echo signal.

Figure 4:
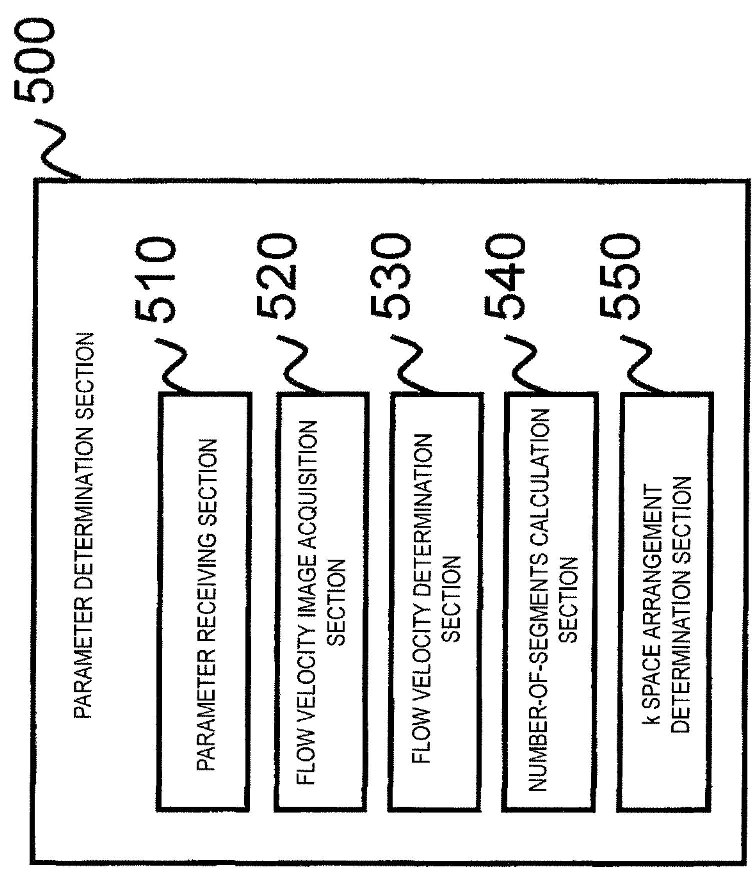
FIG. 4 is a functional block diagram of a parameter determination section of the first embodiment.

FIG. 4 is a functional block diagram of the parameter determination section 500 of the present embodiment. As shown in this drawing, in order to realize parameter determination processing the parameter determination section 500 includes a parameter receiving section 510, a flow velocity image acquisition section 520, a flow velocity determination section 530, a number-of-segments calculation section 540, and a k-space ordering determination section 550.

The parameter receiving section 510 receives imaging parameters input by the operator. Among the received parameters, imaging parameters relevant to the parameter determination processing executed by the parameter determination section 500 are the position (excitation position) excited by the two-dimensional selective excitation pulse, size (region size) ϕ of a region that is selectively excited, and measurement time $TR_{eff}$ of each segment. These imaging parameters are set by the operator through the display unit 111 and the operating unit 112.

For example, the numerical value of the measurement time $TR_{eff}$ of a segment is set from an imaging parameter setting screen or the like prepared in advance.

Figure 5:
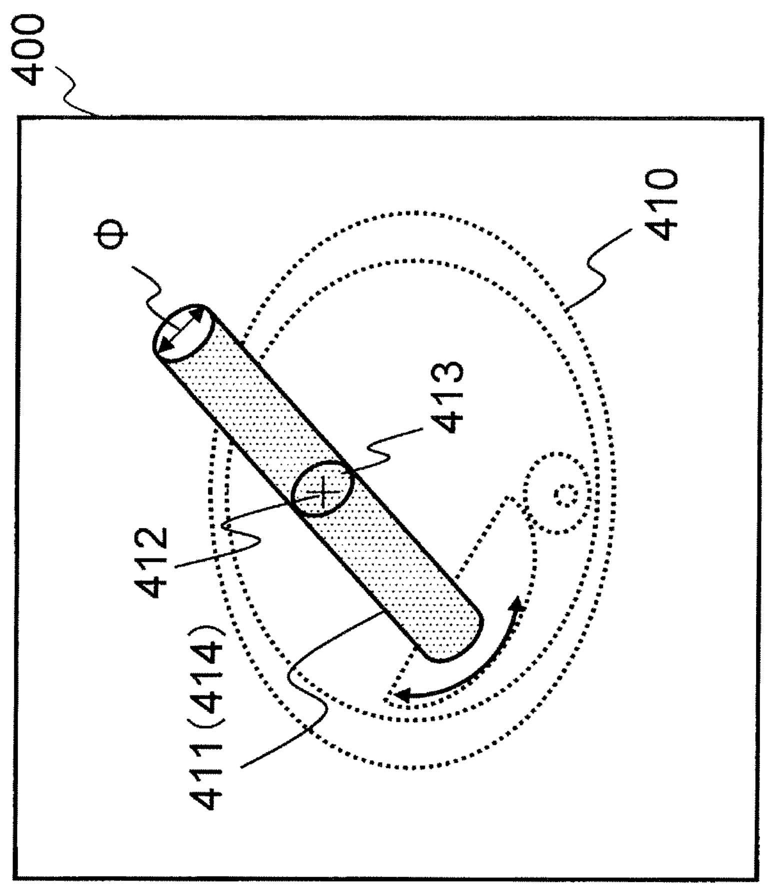
FIG. 5 is an explanatory diagram illustrating an example of a UI screen of the first embodiment.

The inputs of the excitation position and the region size ϕ of the two-dimensional selective excitation pulse are received on a positioning image through a UI (User Interface) for two-dimensional selective excitation region setting prepared in advance. An example of the UI, which is used when the operator sets the excitation position and the region size ϕ on the positioning image, is shown. FIG. 5 shows an example of a GUI screen 400 for inputting the excitation position and the region size ϕ of the two-dimensional selective excitation pulse of the present embodiment.

As shown in this drawing, the operator inputs the region size ϕ and the excitation position with respect to the flow path (here, a blood vessel) of the fluid to be imaged by operating a UI for two-dimensional selective excitation region setting 411 displayed on a positioning image 410. In addition, the region shown by the UI for two-dimensional selective excitation region setting 411 becomes a two-dimensional selective excitation region 414. Here, a point 412 is a labeling point, and the operator sets the labeling point 412 at a position (here, on a blood vessel) where local labeling is desired. The two-dimensional excitation selection UI 411 (two-dimensional selective excitation region 414) enables a setting based on arbitrary position and angle.

In addition, although the cross-sectional shape of the two-dimensional excitation selection UI 411 (two-dimensional selective excitation region 414) is circular in this drawing, the cross-sectional shape is not limited to this. The cross-sectional shape may be set as an arbitrary shape.

The flow velocity image acquisition section 520 acquires a flow velocity image of the fluid to be imaged. The region where the flow velocity image is acquired is a region including across section 413 of the two-dimensional selective excitation region 414. This cross section 413 is a cross section which is perpendicular to the cylindrical axis of the two-dimensional selective excitation region 414 received by the parameter receiving section 510 and which passes through the labeling point 412. In addition, the flow velocity image is acquired by the flow velocity measurement sequence.

As an example of the used flow velocity measurement sequence, a known PC (Phase Contrast) sequence or the like is used. A VENC (velocity encode) pulse used in the PC sequence is applied such that the positive value is in one direction toward the imaging plane in the acquired flow velocity image.

Figure 6:
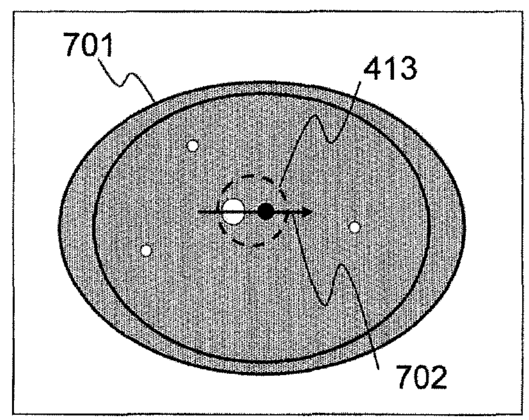
FIG. 6(*a*) is an explanatory diagram illustrating a flow velocity image of the first embodiment, and FIG. 6(*b*) is an explanatory diagram illustrating the line profile of the flow velocity image of the first embodiment.
Figure 6:
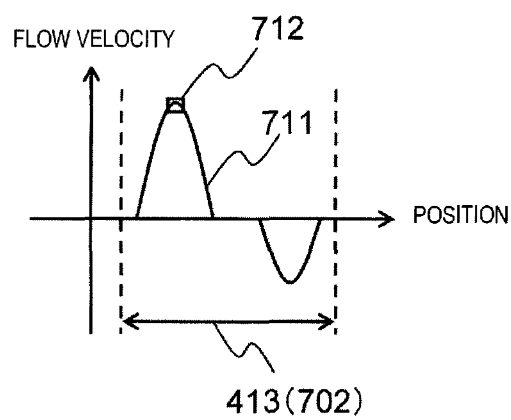

In addition, the flow velocity measurement sequence is executed when the control unit 110 operates each unit of the MRI apparatus 100 according to the pulse sequence stored in advance. Then, the control unit 110 reconstructs the acquired echo signals to obtain a flow velocity image. FIG. 6(*a*) shows a flow velocity image 701 acquired by the flow velocity image acquisition section 520.

The flow velocity determination section 530 determines a flow velocity $V_0$ of the fluid to be imaged from the acquired flow velocity image 701. Here, the flow velocity determination section 530 acquires the profile of the flow velocity on the cross section 413 of the two-dimensional selective excitation region 414, and determines a maximum flow velocity ($V_{max}$) on the profile as the flow velocity $V_0$. FIG. 6(*b*) shows a one-dimensional line profile 711 in a direction of arrow 702 shown in FIG. 6(*a*). The vertical axis indicates the flow velocity, and the horizontal axis indicates the position of the cross section 413 in a direction of the diameter (arrow) 702. A maximum value 712 on the line profile 711 is set as a maximum flow velocity ($V_{max}$), that is, the flow velocity $V_0$.

Here, since a direction perpendicular to the cross section 413 is a direction in which the fluid to be imaged flows, the maximum flow velocity $V_{max}$ in this direction can be regarded as the flow velocity $V_0$ of the fluid to be imaged.

In addition, although the one-dimensional line profile 711 is shown herein in order to simplify the explanation, the profile of the flow velocity that the flow velocity determination section 530 acquires from the flow velocity image 701 is a two-dimensional spatial profile.

The number-of-segments calculation section 540 calculates the number of segments N which is optimal for the imaging. In this calculation, a maximum number among the numbers of segments, to which the two-dimensional selective excitation pulse is applied at least once while the fluid to be imaged passes through the two-dimensional selective excitation region 414, is set as the number of segments N using the flow velocity $V_0$ determined by the flow velocity determination section 530 and the region size ϕ input by the operator. This reason is as follows.

Figure 7:
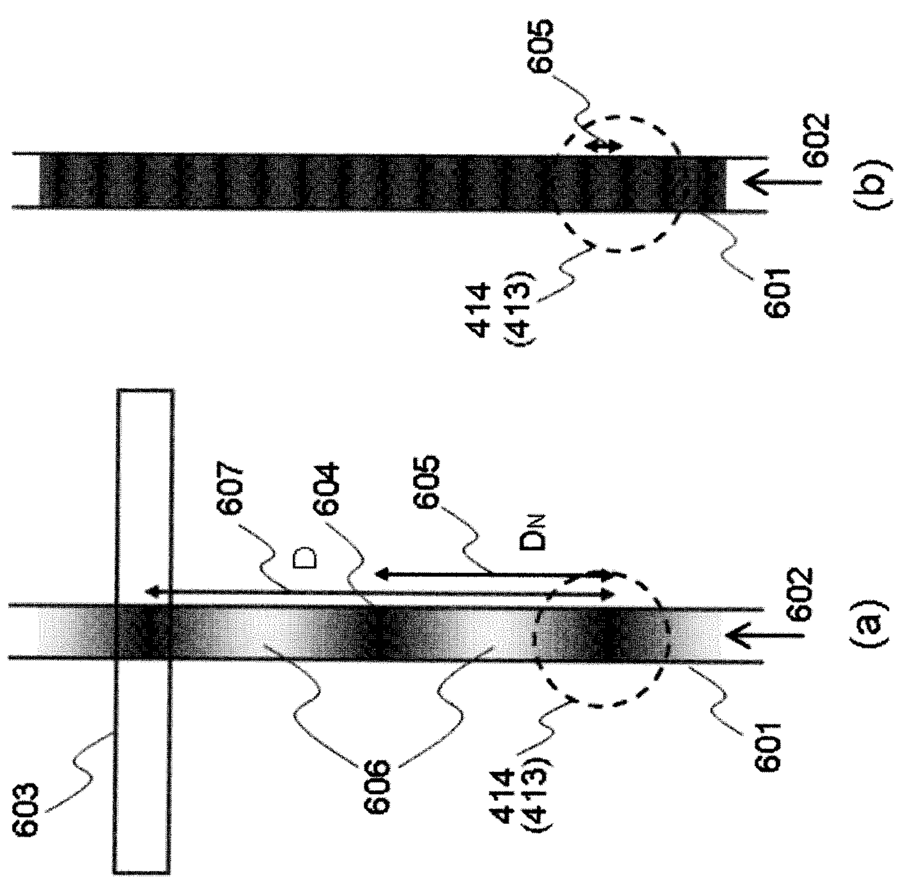
FIGS. 7(*a*) and 7(*b*) are explanatory diagrams illustrating the relationship between the number of segments and the labeling of blood.

FIG. 7 is a diagram illustrating the relationship between the number of segments N and labeling of blood when the fluid to be imaged is blood. FIG. 7(*a*) shows an example when N is a large value, and FIG. 7(*b*) shows an example when N is a smaller value than FIG. 7(*a*). In this drawing, it is assumed that blood flows through a blood vessel 601 in a direction of arrow 602 (blood flow direction). In addition, the image position, the number of segments, and measurement time per segment are set to 603, N, and $TR_{eff}$, respectively.

A distance $D_N$ 605 by which blood (labeling blood) 604, to which the two-dimensional selective excitation pulse is applied in the two-dimensional selective excitation region 414 (cross section 413), travels until the measurement of the N-th segment, which is the last segment executed in one phase 330, ends is expressed as in the following expression (1).

$$D_N = N * TR_{eff} * V_0 \quad (1)$$

As can be seen from expression (1), the travel distance $D_N$ 605 changes with the number of segments N. That is, when the number of segments N is large, the travel distance $D_N$ 605 becomes large as shown in FIG. 7(*a*). In addition, when the number of segments N is small, the travel distance $D_N$ 605 becomes small as shown in FIG. 7(*b*).

This travel distance $D_N$ 605 is also a travel distance until the next two-dimensional selective excitation pulse is applied. As shown in FIG. 7(*a*), when the travel distance $D_N$ 605 is larger than the region size ϕ of the cross section 413 of the two-dimensional selective excitation region 414, blood 606 which is not labeled is generated. On the contrary, when the travel distance $D_N$ 605 is smaller than the region size ϕ, the blood 606 which is not labeled is not generated. In addition, the blood is labeled since the two-dimensional selective excitation pulse is applied several times while traveling the inside of the cross section 413.

Thus, the smaller the travel distance $D_N$ 605 is than the region size ϕ, the more number of times can the blood receive the application of the two-dimensional selective excitation pulse while the blood travels the region size ϕ.

That is, as the number of segments N decreases, stable labeling can be performed. Therefore, in order to perform stable labeling, the smaller number of segments N, the better. On the other hand, since the number of times of the application of the two-dimensional selective excitation pulse increases as the number of segments N decreases, the imaging time shortening effect is small. Therefore, in order to increase the imaging time shortening effect, the larger number of segments N, the better. From these circumstances, it can be seen that the maximum value, among all numbers by which the fluid to be imaged is labeled, is preferably adopted as the number of segments N.

Assuming that the two-dimensional selective excitation pulse is applied at least once while the fluid to be imaged passes through the two-dimensional selective excitation region 414, it is preferable that the travel distance $D_N$ 605 be equal to or less than the diameter as shown in the following expression (2).

$$D_N \leq \phi \quad (2)$$

The relational expression of the following expression (3) is obtained by substituting the above-described expression (1) into expression (2).

$$N \leq \phi / TR_{eff} / V_0 \quad (3)$$

The number-of-segments calculation section 540 sets the maximum integer satisfying expression (3) as the number of segments N.

The k-space ordering determination section 550 determines the k-space ordering of echo signals, that is, k-space ordering, so that echo signals with the higher label effect are arranged in the low spatial frequency region of k space. Hereinafter, the lowest spatial frequency region of k space is called the center.

An echo signal of the segment with the highest label effect in each phase 330 is arranged near the center of k space. For this reason, the k-space ordering determination section 550 first specifies the segment number of the segment with the highest label effect in each phase 330.

As shown in FIG. 7 (*a*), assuming that a distance 607 from the position (two-dimensional selective excitation region 414) of labeling in the fluid to be imaged to the imaging position 603 is D, the labeled fluid arrives at the imaging position 603 at a timing satisfying expression (4). Here, "a" is the real number.

$$D = a * TR_{eff} * V_0 \quad (4)$$

Therefore, the segment number n of the segment in which the highest labeling effect is obtained becomes an integer closest to a that satisfies expression (5) obtained by transforming expression (4).

$$a=D/TR_{eff}/V_0 \quad (5)$$

In addition, when N<n is satisfied, that is, when the timing at which the fluid to which the pre-pulse is applied arrives at the imaging position 603 exceeds TR shown in FIG. 3, waiting time TI is added to the elapsed time ($a*TR_{eff}$) in expression (4). That is, the following expression (6) is used instead of expression (4).

$$D=(a*TR_{eff}+TI)*V_0 \quad (6)$$

When the segment number n of the segment arranged at the center of k space is determined, the k-space ordering determination section 550 also determines the arrangement of other echo signals so that echo signals of the segment number n in each phase 330 are arranged near the center of k space. In the present embodiment, the arrangement of other echo signals is determined so that other echo signals are arranged at positions closer to the center since the closer the number is to the determined segment number n, the higher is the labeling effect. In addition, a change in the amount of application of the encoding pulse (gradient magnetic field) is determined so as to realize the determined k-space ordering. In addition, the determined amount of application of the encoding pulse is reflected in the pulse sequence as an imaging parameter, and the control unit 110 executes imaging according to the pulse sequence.

Figure 8:
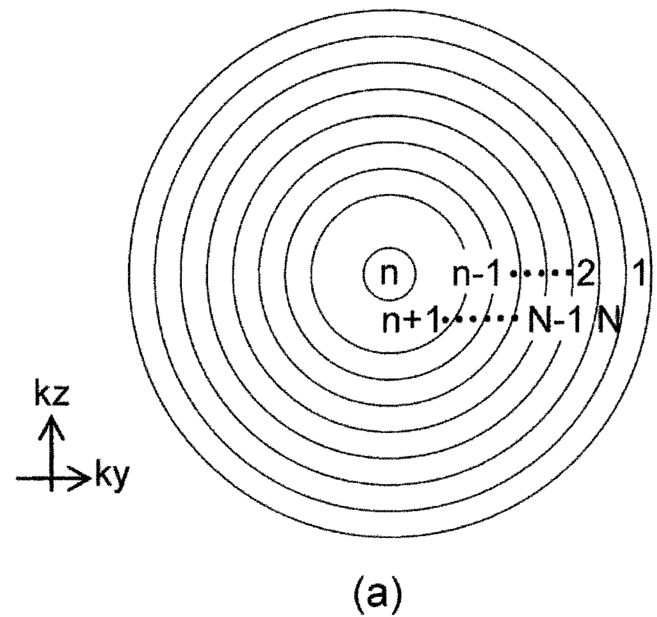
FIGS. 8(*a*) and 8(*b*) are explanatory diagrams illustrating the k-space ordering of the first embodiment.
Figure 8:
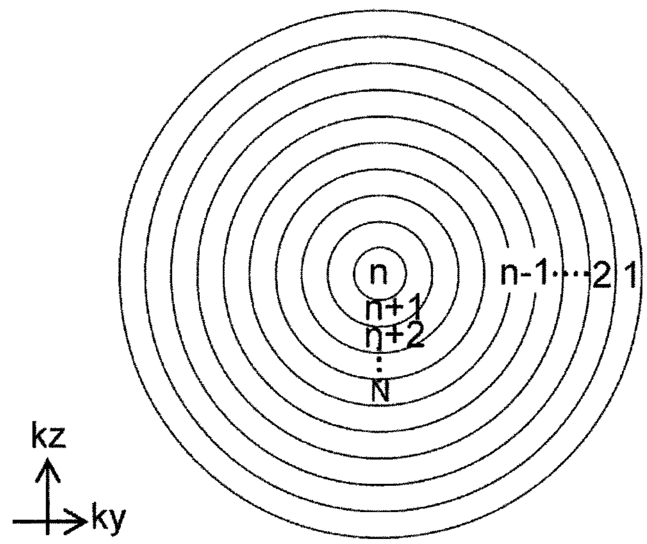

Here, a specific example of the k-space ordering determined by the k-space ordering determination section 550 will be described with reference to FIG. 8(*a*). Here, a case where the number of repetitions of the phase 330 is 1 is illustrated. For example, ky-kz space (y is a phase encoding direction and z is a slice encoding direction) is set ask space. The first to n-th segments are arranged in this order so as to become close to the center of k space. In addition, the (n+1)-th to N-th segments are arranged toward the outside from the center of k space. The k-space ordering determination section 550 determines the amount of encoding pulse application (k-space ordering) so as to realize these arrangements.

In addition, when the total number of encoding is P (P is an integer) and the number of segments is N, the number of repetitions M (M is an integer) of the phase 330 is expressed as P/N. In addition, when P is not an integral multiple of N, M is an integer rounded up. Preferably, echo signals of the segment number n in which the highest labeling effect is obtained are arranged near the center of k space in all M times.

Figure 9:
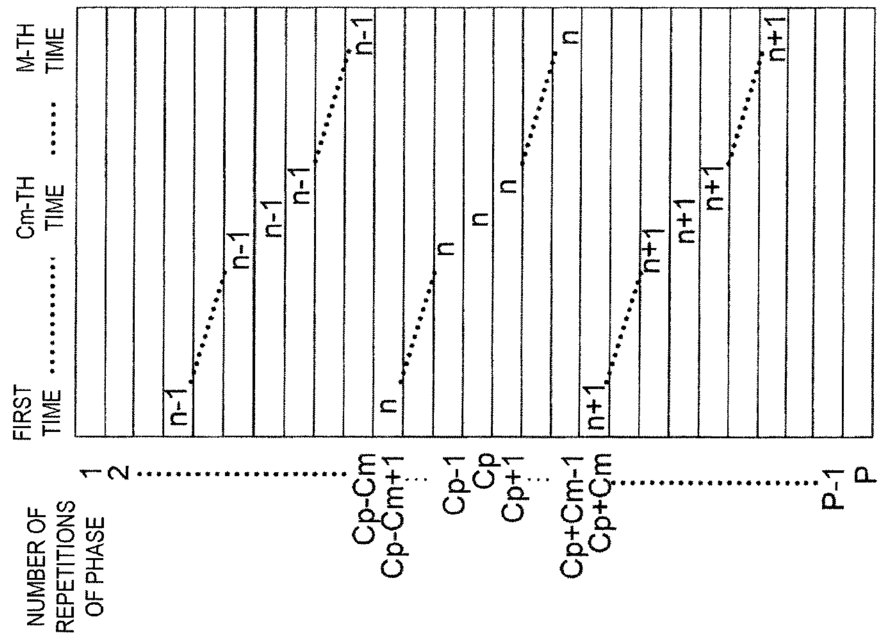
FIG. 9 is an explanatory diagram illustrating the k-space ordering of the first embodiment.

FIG. 9 shows an example of the arrangement. The encoding number of the center of k space is set as Cp. This Cp is a value of the center of the encoding number P, and is an integer obtained by rounding off P/2. In addition, the center Cm of M measurements is similarly set to an integer obtained by rounding off M/2.

The echo signal obtained in the n-th segment in the Cm-th phase 330 is arranged in the Cp-th phase which is the center of k space. In addition, the echo signal of the n-th segment in the (Cm+1)-th measurement is arranged in the (Cp+1)-th phase, and the echo signal of the n-th segment in the (Cm−1)-th measurement is arranged in the (Cp−1)-th phase. Thus, echo signals are centrically arranged for each phase 330 and each segment number.

Figure 10:
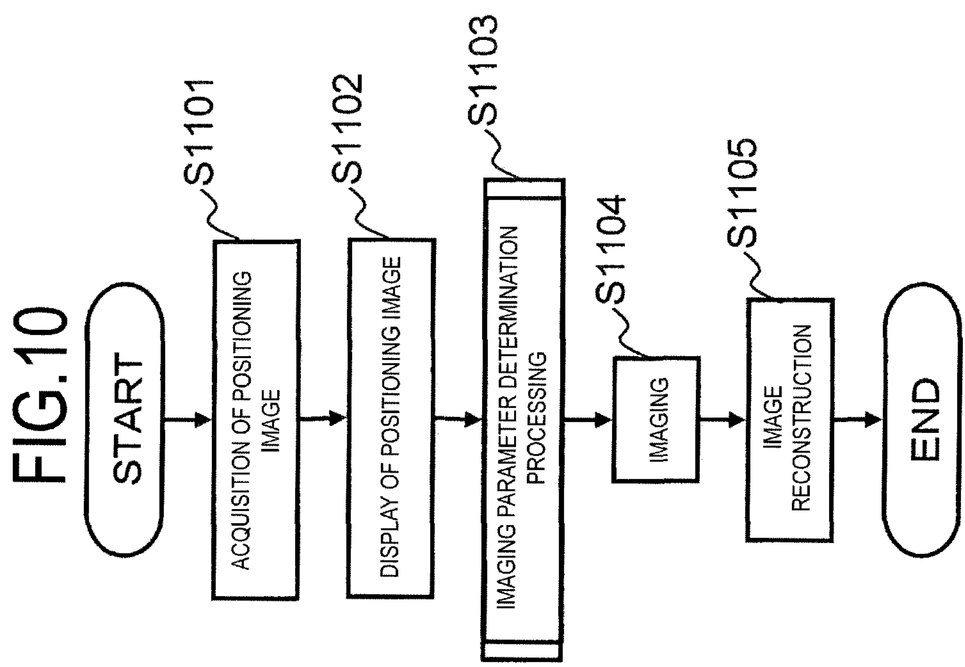
FIG. 10 is a flow chart of imaging processing of the first embodiment.

Next, FIG. 10 illustrating the flow of the imaging processing of the control unit 110 of the present embodiment using each of the above-described sections is a process flow of imaging processing of the present embodiment.

First, the control unit 110 acquires a positioning image (step S1101). The positioning image is acquired by operating the MRI apparatus 100 using the pulse sequence set in advance to acquire the positioning image 410.

After the positioning image 410 is acquired, the control unit 110 generates an imaging parameter setting screen and the GUI screen 400 using the positioning image 410 and displays them on the display unit 110 (step S1102), and makes the parameter determination section 500 perform imaging parameter determination processing (step S1103). Here, the parameter determination section 500 receives the inputs of imaging parameters including $TR_{eff}$ which is the measurement time per segment, imaging position, and excitation position and region size ϕ of a two-dimensional selective excitation region, and determines the number of segments N and the k-space ordering (amount of encoding pulse application).

After the parameter determination section 500 determines the number of segments N and the k-space ordering (the amount of encoding pulse application), the control unit 110 performs imaging by executing the pulse sequence, which is set in advance for imaging, in the determined k-space ordering (the amount of encoding pulse application) by the determined number of segments N (step S1104).

Then, the control unit 110 reconstructs an image by performing a Fourier transform of the acquired echo signal (step S1105).

In addition, the inputs of imaging parameters which do not need to be received on the positioning image may be received before the acquisition of the positioning image.

Figure 11:
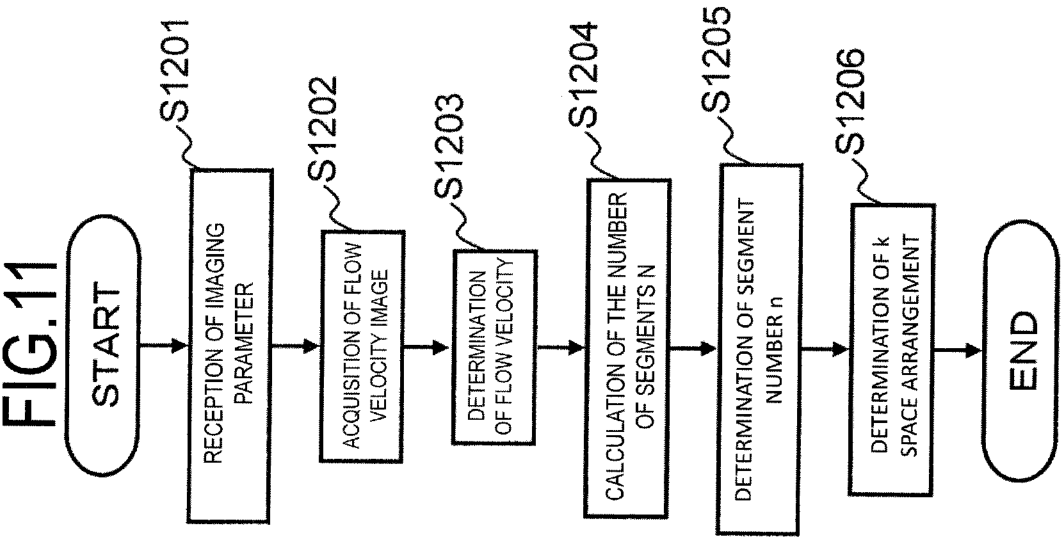
FIG. 11 is a flow chart of imaging parameter determination processing of the first embodiment.

Next, the flow of imaging parameter determination processing performed by the parameter determination section 500 in the above step S1103 will be described. FIG. 11 is a process flow of the imaging parameter determination processing of the present embodiment.

When the operator inputs the excitation position and the region size ϕ of the two-dimensional selective excitation pulse on the positioning image 410, the parameter receiving section 510 receives them together with other imaging parameters including the measurement time $TR_{eff}$ and the imaging position (step S1201).

Then, the flow velocity image acquisition section 520 acquires the flow velocity image 701 of the above-described cross section 413 using the received excitation position and region size ϕ (step S1202).

The flow velocity determination section 530 determines the flow velocity $V_0$ of the fluid to be imaged from the acquired flow velocity image 701 (step S1203).

The number-of-segments calculation section 540 calculates the number of segments N to be adopted using the flow velocity $V_0$ calculated in step S1203, the region size ϕ received in step S1201, and the measurement time $TR_{eff}$ (step S1204).

The k-space ordering determination section 550 first determines the segment number n of the segment in which the highest labeling effect is acquired (step S1205). The segment number n is calculated using the distance D between the imaging position received in step S1201 and the application position of the two-dimensional selective excitation pulse which is calculated from the imaging position and the application position, the calculated flow velocity $V_0$, and the received measurement time $TR_{eff}$. After the segment number n is determined, the k-space ordering determination section 550 determines the k-space ordering (the amount of encoding pulse application) using the number of segments N and the number n (step S1206).

The parameter determination section 500 outputs the calculated number of segments N and the calculated k-space ordering (the amount of encoding pulse application), and ends the processing.

As described above, according to the present embodiment, in the segment measurement to shorten the imaging time by executing a plurality of segments after one application of the pre-pulse (two-dimensional selective excitation pulse), the optimal number of segments is determined according to the flow velocity of the fluid to be imaged and the size of the application region of the two-dimensional selective excitation pulse. The optimal number of segments is calculated as the maximum number by which the two-dimensional selective excitation pulse is applied at least once to the fluid within the two-dimensional selective excitation region to which the two-dimensional selective excitation pulse is applied.

Therefore, according to the present embodiment, it is possible to automatically determine the optimal number of segments N according to the flow velocity of the fluid to be imaged and perform imaging. For this reason, problems, such as the occurrence of artifacts or a contrast reduction due to insufficient labeling, do not occur. In addition, a problem does not occur in which the imaging time becomes long due to the large number of segments. In addition, since the pre-pulse is applied in a two-dimensional selective manner, the effect of the pre-pulse can be given to only the desired fluid with high accuracy. In this manner, only the desired fluid can be drawn with high contrast.

That is, according to the present embodiment, it is possible to obtain the maximum suppression effect within a short imaging time. Therefore, it is possible to efficiently acquire a high-quality image.

In order to apply the pre-pulse in a two-dimensional selective manner, only the fluid of a local region is excited. When the fluid of a local region is labeled as described above, it is necessary to acquire the data while the labeled fluid is passing the imaging range. Accordingly, the accuracy of time from labeling to data acquisition is very important. However, the arrival timing of the fluid to the imaging region changes with the flow velocity V. Therefore, if the data acquisition timing according to the flow velocity V is not optimized, the labeling effect cannot be obtained, and the image contrast is reduced.

In the conventional slice-selective pre-pulse, a time for which the inverted fluid is present within the imaging plane is extended by increasing the slice thickness. However, since the selectivity of a region is lowered if the diameter of a cylinder is increased in the same manner as when labeling only the fluid of a specific region using a two-dimensional selective excitation pulse as the pre-pulse, it is not preferable to apply this method.

According to the present embodiment, it is calculated from the flow velocity the fluid excited in which segment arrives at the imaging plane, and the k-space ordering (the amount of encoding pulse application) is optimized so that the data is located at the center of ky-kz space. That is, in the present embodiment, the amount of encoding pulse application (k-space ordering) is determined so that echo signals of the segment, in which the highest labeling effect is obtained, are arranged at the center of k space. Accordingly, it is possible to acquire a high-quality image with the greater effect of pre-pulse (two-dimensional selective excitation pulse).

For example, in the case of vasodepression imaging, the optimal number of segments N is automatically determined from the blood flow velocity, the cylinder diameter of the two-dimensional selective excitation region, and the repetition time $TR_{eff}$. In this case, the blood flow velocity is automatically calculated from a prescan or a pre-measurement result. In addition, a segment in which the blood vessel is suppressed most is determined from the blood flow velocity, and the k-space ordering is optimized so that echo signals obtained in the segment are located at the center of k space.

In addition, although the maximum flow velocity $V_{max}$ in the flow velocity image 701 is set as the flow velocity $V_0$ of the fluid to be imaged and the flow velocity $V_0$ is fixed in the embodiment described above, the determination of the flow velocity is not limited to this method. For example, when the fluid to be imaged is blood, imaging using the flow velocity measurement sequence (PC sequence) may be performed at multiple time phases covering one cardiac beat, and the flow velocity may be set as a function V(t) of time t. In this case, the above expression (1) is expressed as the following expression (7).

$$D_N=\int_0^{N*TR_{eff}}V(t)dt \quad (7)$$

In addition, the above expression (4) is expressed as the following expression (8).

$$D=\int_0^{a*TR_{eff}}V(t)dt \quad (8)$$

The number of segments N and the segment number n are determined using these $D_N$ and D.

Figure 12:
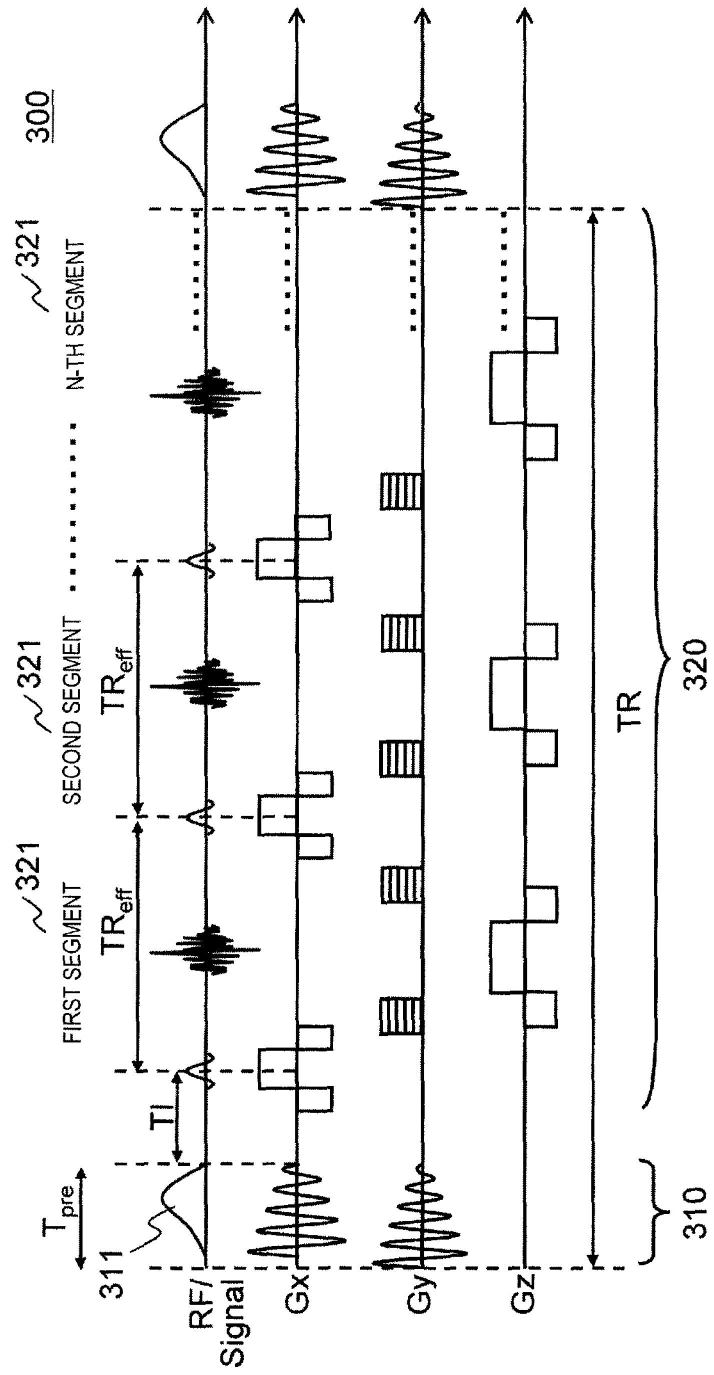
FIG. 12 is an explanatory diagram illustrating another example of the pulse sequence of the first embodiment.

In addition, although the simple GE (Gradient echo) sequence is illustrated as a sequence applied to each segment in the embodiment described above, the application sequence is not limited to this. For example, it is also possible to use the SSFP (Steady State Free Precision) sequence shown in FIG. 12.

This SSFP sequence is a sequence of performing two-dimensional imaging of a desired region (slab region) by making the magnetization in a steady state (SSFP) by repeating the irradiation of RF pulses in a repetition time shorter than the longitudinal relaxation time T1 of the magnetization of the tissue in the fluid to be imaged.

In addition, in the embodiment described above, echo signals acquired in the segment (n-th segment) with the highest labeling effect are arranged in a central region (lowest spatial frequency region) of k space, and the first to n-th segments are arranged so as to be closer to the center of k space in this order and the (n+1)-th to N-th segments are arranged toward the outside from the center of k space. However, as shown in FIG. 8(*b*), a configuration is also possible in which segments are arranged at the center of k space as the segment position becomes closer to the second half of the pulse sequence.

This is because the contrast between the fluid and the stationary tissue is improved as the segment position becomes closer to the TR of the second half of the pulse sequence. That is, the pulse sequence 300 shown in FIG. 3 is repeated in actual imaging. This is because, in the case of a pulse sequence in which echo signals are continuously acquired in such a short TR, signals from the stationary tissue are reduced in proportion to TR of the second half of the pulse sequence and the fluid whose signal is not changed flows into the region. The reason why signals of stationary tissue are reduced is that RF pulses are continuously applied to the same tissue.

By adopting a configuration to scan k space as described above, it is possible to obtain the better contrast.

In addition, although 3D imaging is assumed in the embodiment described above, the present invention is not limited to this. 2D imaging may also be used. In this case, arrangement is performed only in the ky direction using ky space instead of ky-kz space.

In addition, although the k-space ordering determination section 550 is provided to determine the optimal segment number n in the embodiment described above, this configuration may not be adopted. For example, when N is sufficiently small as 2, there is no difference in the effect of the pre-pulse between segments. Accordingly, the sufficient effect is obtained just by calculating the optimal number of segments N and configuring the pulse sequence on the basis of the calculated optimal number of segments N to perform imaging.

<<Second Embodiment>>

Next, a second embodiment to which the present invention is applied will be described. In the present embodiment, an IR pulse (whose excitation angle is equal to or greater than 90° and equal to or less than 180°) is used as an RF pulse for two-dimensional selective excitation of a two-dimensional selective excitation pulse that is used as a pre-pulse. The configuration of the MRI apparatus of the present embodiment is basically the same as that of the MRI apparatus 100 of the first embodiment. Hereinafter, the present embodiment will be described focusing on the different configuration from the first embodiment.

When the IR pulse is used as an RF pulse for two-dimensional selective excitation, it is important to match the timing of actual imaging with the Null point. In addition, since the Null point is a point at which the signal strength becomes 0, a time from the application of the IR pulse to the Null point is called a Null time.

In the case of a normal slice-selective IR pulse, it is possible to increase a time, for which the inverted fluid is present within the imaging plane, by increasing the slice thickness. In the present embodiment, however, a two-dimensional selective excitation pulse is applied as the pre-pulse to excite only the fluid of a local region. In such a case, increasing the slice thickness is not preferable since it lowers the selectivity of a region.

In the present embodiment, the timing of actual imaging and the Null point of the fluid are matched with each other by adjusting the flip angle (FA) of the IR pulse. Here, it will be described that the Null point is moved by adjusting the FA.

Figure 13:
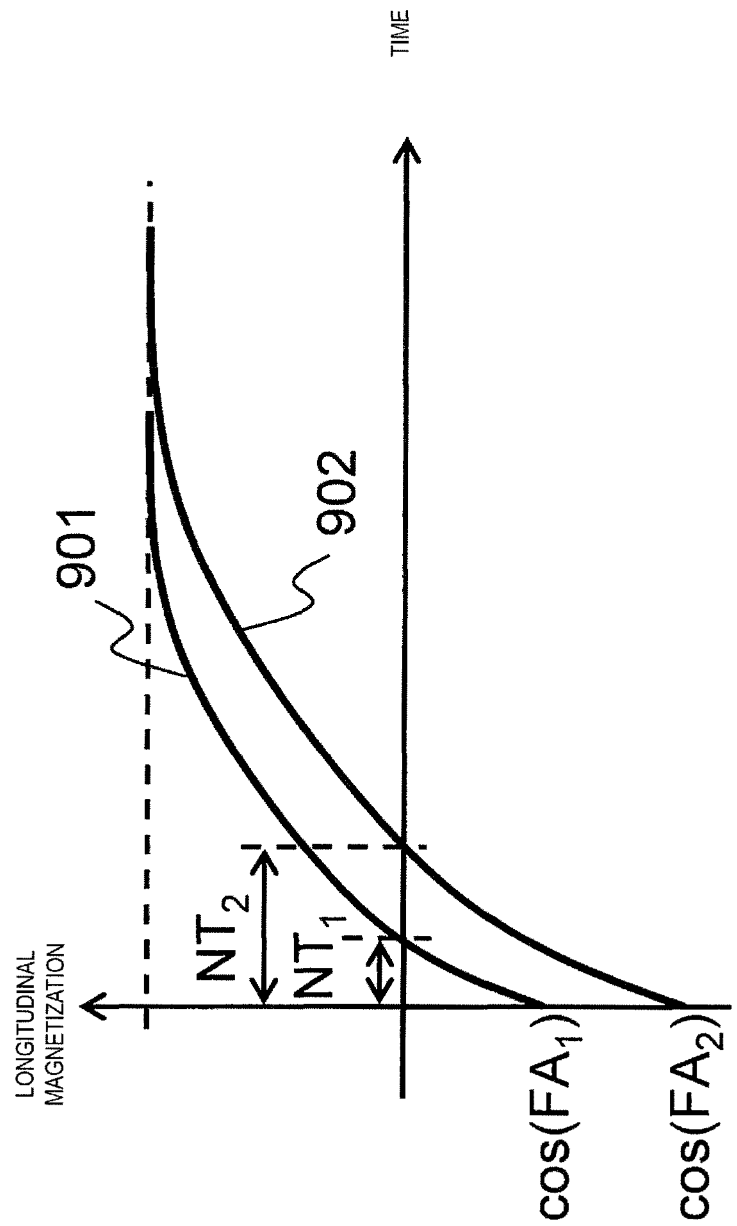
FIG. 13 is an explanatory diagram illustrating the recovery curves of IR pulses of two different flip angles.

FIG. 13 shows the recovery curves of IR pulses of two different flip angles FA ($FA_1<FA_2$). 901 is a recovery curve when the IR pulse whose flip angle is $FA_1$ is applied, and 902 is a recovery curve when the IR pulse whose flip angle is $FA_2$ is applied. In addition, $NT_1$ is a Null time of the IR pulse whose flip angle is $FA_1$, and $NT_2$ is a Null time of the IR pulse whose flip angle is $FA_2$.

As shown in this drawing, when inverting the fluid with the IR pulse of the FA in the relationship of $FA_1<FA_2$, the Null time $NT_1$ of the $FA_1$ is shorter than the Null time $NT_2$ of the $FA_2$. Thus, the Null time changes with the flip angle FA.

Figure 14:
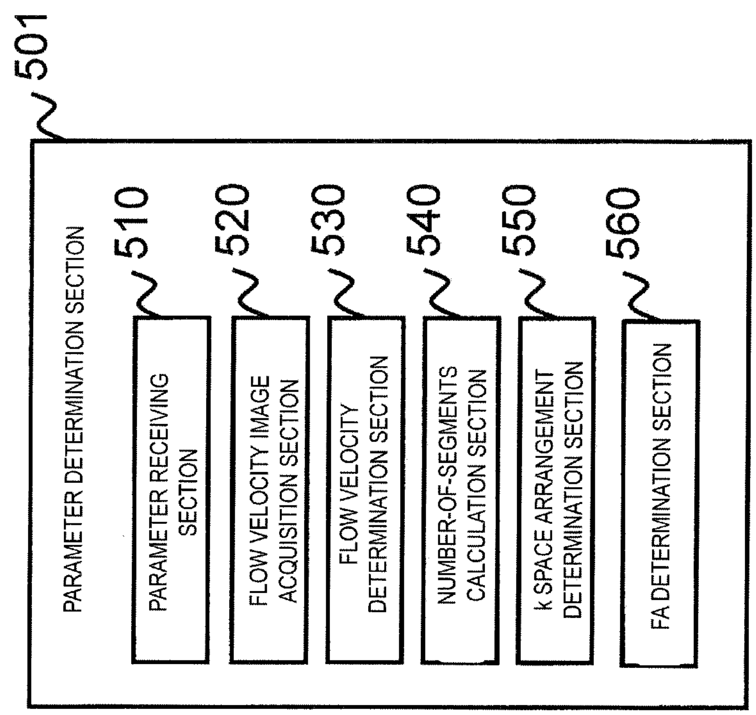
FIG. 14 is a functional block diagram of a parameter determination section of a second embodiment.

Therefore, a parameter determination section 501 of the present embodiment includes an FA determination section 560, which determines the optimal flip angle FA for the IR pulse, in addition to the configuration of the first embodiment. FIG. 14 is a functional block diagram of the parameter determination section 501 of the present embodiment.

The FA determination section 560 determines the optimal flip angle FA (hereinafter, referred to as $FA_{pre}$) of the IR pulse so that the timing of actual imaging and the Null point of the fluid match each other. The optimal flip angle FA is calculated using the flow velocity $V_0$, the distance D between the two-dimensional selective excitation region 414 and the imaging position 603, and the longitudinal relaxation time T1. The calculation method is as follows.

The time TI until the fluid inverted by the IR pulse in the two-dimensional selective excitation region 414 arrives at the imaging position 603 is expressed as in the following expression (9) using the distance D and the flow velocity $V_0$.

$$TI=D/V_0 \tag{9}$$

In addition, longitudinal magnetization $M_{pre}$ immediately after the IR pulse whose flip angle FA is $FA_{pre}$ is applied can be expressed as in the following expression (10) using a net magnetization vector $M_0$.

$$M_{pre}=M_0\cos(FA_{pre}) \tag{10}$$

A change M(t) according to the time t of subsequent longitudinal magnetization can be expressed as in the following expression (11) using the T1 value of the fluid to be imaged.

$$M(t)=1-(1+M_{pre})e^{-t/T1} \tag{11}$$

Therefore, from the above expressions (9), (10), and (11), the value of $FA_{pre}$ that becomes Null (signal strength 0) at t=TI can be calculated as in expression (12).

$$FA_{pre}=\arccos\left(e^{D/V0/T1}-1\right) \tag{12}$$

In addition, in order to satisfy expression (12), the distance D, the flow velocity $V_0$, and $T_1$ need to satisfy the relationship of the following expression (13).

$$-1\leq e^{D/V0/T1}-1\leq+1 \tag{13}$$

The FA determination section 560 sets the $FA_{pre}$ obtained by expression (12) to the flip angle FA of the IR pulse.

Figure 15:
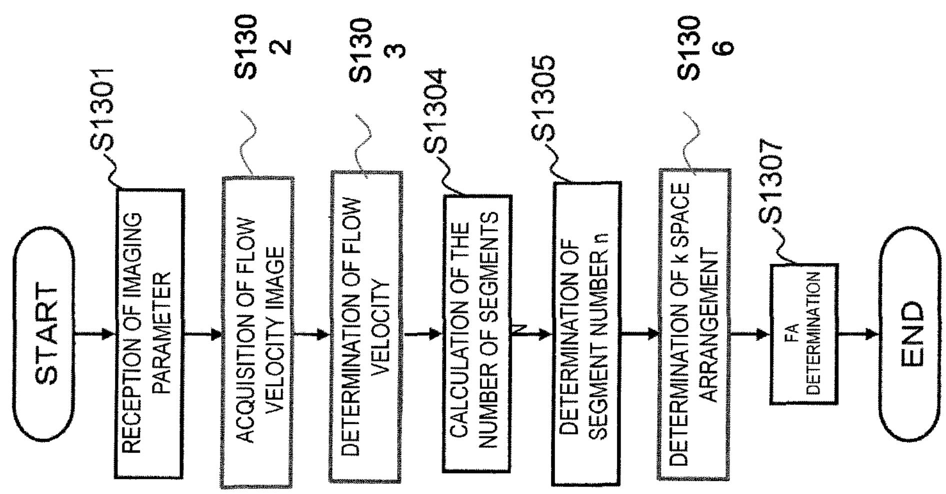
FIG. 15 is a flow chart of parameter determination processing of the second embodiment.

Next, imaging parameter determination processing performed by the parameter determination section 501 of the present embodiment will be described. FIG. 15 is a process flow of the photographing parameter determination processing of the present embodiment.

The imaging parameter determination processing of the present embodiment is basically the same as that of the first embodiment. That is, the parameter receiving section 510 first receives various parameters required for the processing (step S1301). Then, the flow velocity image acquisition section 520 acquires a flow velocity image (step S1302), and the flow velocity determination section 530 determines the flow velocity $V_0$ (step S1303).

Then, the number-of-segments calculation section 540 calculates the number of segments N (step S1304), and the k-space ordering determination section 550 determines the segment number n (step S1305) and then determines the amount of phase encoding application (k-space ordering) (step S1306).

Then, in the present embodiment, the FA determination section 560 determines the optimal FA ($FA_{pre}$) for the IR pulse further using the above-described method (step S1307).

The parameter determination section 500 outputs the calculated number of segments N, the amount of phase encoding application (k-space ordering), and the FA ($FA_{pre}$) of IR pulse, and ends the processing.

In addition, the determination of $FA_{pre}$ by the FA determination section 560 may be performed at any time after step S1303.

In addition, the imaging processing performed by the control unit 110 of the present embodiment is basically the same as that of the first embodiment. However, in step S1104, the control unit 110 executes a pulse sequence using the number of segments N, the k-space ordering (the amount of encoding pulse application), and the $FA_{pre}$ of the IR pulse, which have been determined by the parameter determination section 501.

As described above, according to the present embodiment, even if the IR pulse is used as an RF pulse for two-dimensional selective excitation of a two-dimensional selective excitation pulse that is used as a pre-pulse, it is possible to execute imaging with the maximum number of segments N while giving the maximum pre-pulse effect to the desired fluid with high accuracy as in the first embodiment. Therefore, it is possible to acquire a high-quality image at high speed.

In addition, in expressions (12) and (13), the flow velocity $V_0$ is a value determined by the state of the object, and the T1 value is a value determined by the state of the fluid and the strength of the static magnetic field. Accordingly, only the distance D can be changed in expressions (12) and (13). When the solution of expression (12) cannot be obtained with the set distance D, the control unit 110 may calculate the range $D_{scope}$ of the distance D satisfying expression (13) and present the calculated range $D_{scope}$ on the positioning image. The operator can adjust the distance D by viewing this display. In addition, restrictions may be set such that, when the operator sets the two-dimensional selective excitation region 414 on the positioning image, the set two-dimensional selective excitation region 414 is not accepted if the set two-dimensional selective excitation region 414 deviates from the range $D_{scope}$ of the distance D.

Figure 16:
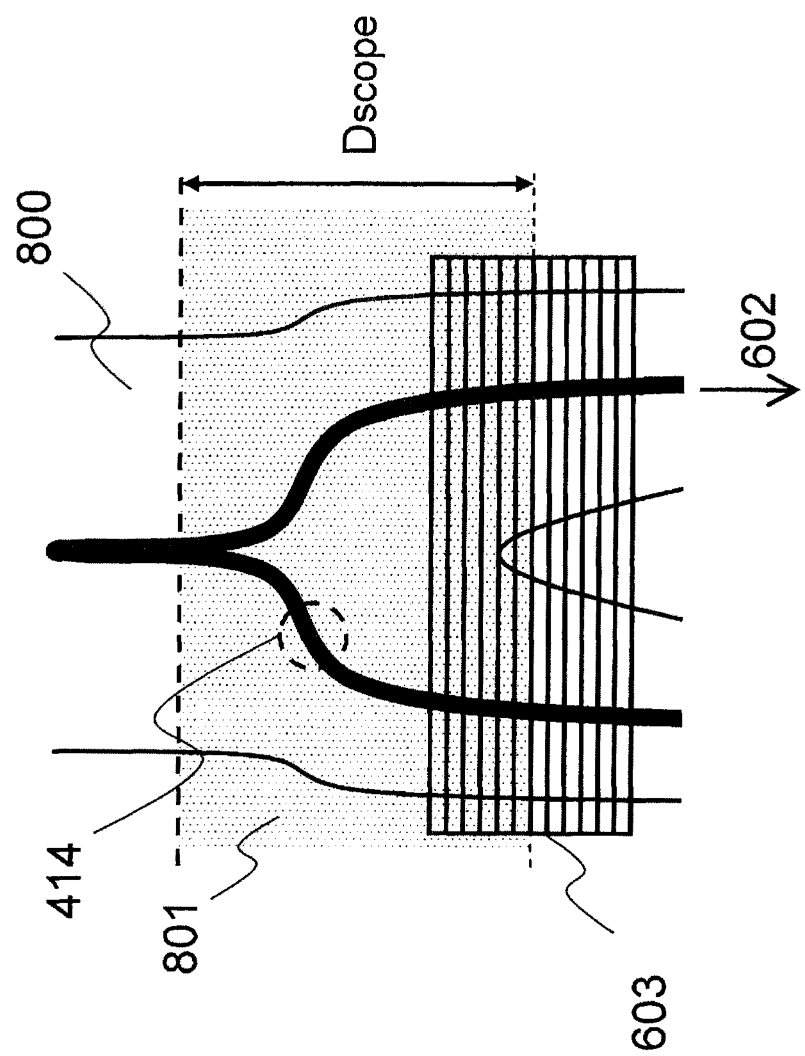
FIG. 16 is an explanatory diagram illustrating a positioning image for two-dimensional selective excitation region setting of the second embodiment.

FIG. 16 shows a display example of a positioning image 800 in this case. In this drawing, 801 is the range $D_{scope}$ of the distance D satisfying expression (12). In addition, 602 is a blood flow direction. For the imaging position 603, the operator can set the two-dimensional selective excitation pulse application position, that is, the two-dimensional selective excitation position 414 only in this range 801.

In addition, although the parameter determination sections 500 and 501 are provided in the control unit 110 in each of the embodiments described above, the present invention is not limited to this. The parameter determination sections 500 and 501 may also be provided in an external information processing apparatus that can transmit and receive data to and from the MRI apparatus 100.

The features of the present invention described in each of the above embodiments can be summarized as follows.

That is, an MRI apparatus of the present invention is an MRI apparatus that acquires an image of a fluid by dividing k space into a plurality of segments, applying a two-dimensional selective excitation pulse as a pre-pulse, and measuring echo signals of one or more segments each time the two-dimensional selective excitation pulse is applied. The MRI apparatus includes: an imaging parameter determination unit that determines the number of segment execution times, which is the number of segments measured each time the two-dimensional selective excitation pulse is applied, from a velocity of a fluid to be imaged, a size of an excitation region of the input two-dimensional selective excitation pulse, and measurement time per segment.

Preferably, the imaging parameter determination unit includes a velocity determination section that determines a velocity of the fluid to be imaged and a number-of-segment-execution-times calculation section that calculates the number of segment execution times. The number-of-segment-execution-times calculation section determines the maximum number of segments, among the numbers of segments to which the two-dimensional selective excitation pulse is applied at least once while the fluid to be imaged passes through the excitation region of the two-dimensional selective excitation pulse, as the number of segment execution times from the velocity determined by the velocity determination section, the size of the excitation region of the two-dimensional selective excitation pulse, and the measurement time per segment.

In addition, preferably, the number-of-segment-execution-times calculation section determines the number of segment execution times by dividing the size of the excitation region of the two-dimensional selective excitation pulse by the velocity of the fluid to be imaged and the measurement time per segment.

In addition, preferably, the imaging parameter determination unit includes a velocity determination section that determines a velocity of the fluid to be imaged and a number-of-segment-execution-times calculation section that calculates the number of segment execution times, and the velocity determination section includes a flow velocity image acquisition section that acquires a flow velocity image of the fluid to be imaged and a flow velocity determination section that determines a flow velocity of the fluid to be imaged from the flow velocity image.

In addition, preferably, a two-dimensional selective excitation region excited by the two-dimensional selective excitation pulse has a cylindrical shape, the flow velocity image acquisition section acquires the flow velocity image of a cross section, which is within a flow path of the fluid to be imaged and is perpendicular to the cylindrical axis of the two-dimensional selective excitation region, and the flow velocity determination section determines, as the flow velocity of the fluid to be imaged, a maximum flow velocity on a profile of the flow velocity image in a flow path direction of the fluid to be imaged.

In addition, preferably, the fluid to be imaged is blood, the flow velocity image acquisition section acquires the flow velocity image at multiple time phases covering one cardiac beat, and the flow velocity determination section interpolates the maximum flow velocity of each flow velocity image and determines the flow velocity as a function of time.

In addition, preferably, the imaging parameter determination unit further includes a k-space ordering determination section that determines an echo signal acquired in each segment such that an echo signal with a greater effect of the two-dimensional selective excitation pulse is arranged in a region closer to the center of k space.

In addition, preferably, the k-space ordering determination section determines a segment, in which an echo signal with a greatest effect of the two-dimensional selective excitation pulse is acquired, from the velocity of the fluid to be imaged and the measurement time per segment and arranges the echo signal near the center of k space.

In addition, preferably, the k-space ordering determination section determines a segment, in which an echo signal with a greatest effect of a pre-pulse is acquired, by dividing a distance between an application position of the two-dimensional selective excitation pulse and an imaging position by the velocity determined by the velocity determination section and the measurement time per segment.

In addition, preferably, an RF pulse used as the two-dimensional selective excitation pulse is an IR pulse, the imaging parameter determination unit further includes a flip angle determination section that determines a flip angle of the IR pulse, and the flip angle determination section calculates the flip angle such that a time taken for the fluid to be imaged to travel by a distance between an application position of the IR pulse and an imaging position becomes an inversion time of the IR pulse using the velocity of the fluid to be imaged.

In addition, preferably, the imaging parameter determination unit further includes a distance calculation section that, when the flip angle determination section is not able to calculate the flip angle, calculates the distance between the application position of the IR pulse and the imaging position from which the flip angle can be calculated and presents the calculated distance to an operator.

In addition, a fluid imaging method of the present invention is a fluid imaging method of acquiring an image of a fluid by dividing k space into a plurality of segments, applying a two-dimensional selective excitation pulse as a pre-pulse, and measuring echo signals of one or more segments each time the two-dimensional selective excitation pulse is applied using a magnetic resonance imaging apparatus. The fluid imaging method includes: an imaging parameter determination step of determining the number of segment execution times, which is the number of segments measured each time the two-dimensional selective excitation pulse is applied, from a velocity of a fluid to be imaged, a size of an excitation region of the input two-dimensional selective excitation pulse, and measurement time per segment; a measurement step of measuring echo signals of each segment by the number of segment execution times and arranging the acquired echo signals in k space each time the two-dimensional selective excitation pulse is applied; and an image reconstruction step of reconstructing an image from the echo signals arranged in k space.

Preferably, a positioning image acquisition step of acquiring a positioning image is further provided before the imaging parameter determination step. The imaging parameter determination step includes a parameter receiving step of receiving inputs of the measurement time per segment and the size of the excitation region of the two-dimensional selective excitation pulse on the positioning image, a velocity determination step of calculating the velocity of the fluid to be imaged, and a number-of-execution-times determination step of determining the maximum number of segments, among the numbers of segments to which the two-dimensional selective excitation pulse is applied at least once while the fluid to be imaged passes through the excitation region of the two-dimensional selective excitation pulse, as the number of segment execution times from the velocity of the fluid to be imaged, the size of the excitation region of the two-dimensional selective excitation pulse, and the measurement time per segment.

REFERENCE SIGNS LIST

100: MRI apparatus
101: object
102: magnet
103: gradient magnetic field coil
104: RF coil
105: RF probe
106: gradient magnetic field power source
107: RE transmission unit
108: signal detection unit
109: signal processing unit
110: control unit
111: display unit
112: operating unit
113: bed
200: pulse sequence
210: pre-pulse portion
211: IR pulse
212: two-dimensional selective excitation pulse
213: two-dimensional selective excitation pulse
214: pre-saturation pulse
215: gradient magnetic field
220: actual imaging portion
221: RF pulse
222: slice selection gradient magnetic field
223: phase encoding gradient magnetic field
224: reading encoding gradient magnetic field
225: echo signal
300: pulse sequence
310: pre-pulse portion
311: RF pulse for two-dimensional selective excitation
312: gradient magnetic field pulse for two-dimensional selective excitation
313: gradient magnetic field pulse for two-dimensional selective excitation
320: actual imaging portion
321: segment
330: phase
400: GUI screen
410: positioning image
411: two-dimensional excitation selection UI
412: labeling point
413: cross section
414: two-dimensional selective excitation region
500: parameter determination section
501: parameter determination section
510: parameter receiving section
520: flow velocity image acquisition section
530: flow velocity determination section
540: number-of-segments calculation section
550: k-space ordering determination section
560: FA determination section
601: blood vessel
602: blood flow direction
603: imaging position
604: labeling blood
605: travel distance
606: blood which is not labeled
607: distance
701: flow velocity image
702: arrow
711: line profile
712: maximum flow velocity
800: positioning image
801: range of distance
901: recovery curve
902: recovery curve

The invention claimed is:

1. A magnetic resonance imaging apparatus that acquires an image of a fluid by dividing k space into a plurality of segments, applying a two-dimensional selective excitation pulse as a pre-pulse, and measuring echo signals of one or more segments each time the two-dimensional selective excitation pulse is applied, the apparatus comprising:

an imaging parameter determination unit that determines the number of segment execution times, which is the number of segments, amongst the plurality of segments of k space, measured each time the two-dimensional selective excitation pulse is applied, from a velocity of a fluid to be imaged, a size of an excitation region of the input two-dimensional selective excitation pulse, and measurement time per segment, wherein the imaging parameter determination unit includes a velocity determination section that determines a velocity of the fluid to be imaged and a number-of-segment-execution-times calculation section that calculates the number of segment execution times, and the velocity determination section includes a flow velocity image acquisition section that acquires a flow velocity image of the fluid to be imaged and a flow velocity determination section that determines a flow velocity of the fluid to be imaged from the flow velocity image, wherein the imaging parameter determination unit further includes a k-space ordering determination section that determines an echo signal acquired in each segment such that an echo signal with a greater effect of the two-dimensional selective excitation pulse is arranged in a region closer to the center of k space, and wherein the k-space ordering determination section determines a segment, in which an echo signal with a greatest effect of the two-dimensional selective excitation pulse is acquired, from the velocity of the fluid to be imaged and the measurement time per segment and arranges the echo signal near the center of k space.

2. The magnetic resonance imaging apparatus according to claim 1, wherein the number-of-segment-execution-times calculation section determines the maximum number of segments, among the numbers of segments to which the two-dimensional selective excitation pulse is applied at least once while the fluid to be imaged passes through the excitation region of the two-dimensional selective excitation pulse, as the number of segment execution times from the velocity determined by the velocity determination section, the size of the excitation region of the two-dimensional selective excitation pulse, and the measurement time per segment.

3. The magnetic resonance imaging apparatus according to claim 2, wherein the number-of-segment-execution-times calculation section calculates the number of segment execution times by dividing the size of the excitation region of the two-dimensional selective excitation pulse by the velocity of the fluid to be imaged and the measurement time per segment.

4. The magnetic resonance imaging apparatus according to claim 1, wherein a two-dimensional selective excitation region excited by the two-dimensional selective excitation pulse has a cylindrical shape, the flow velocity image acquisition section acquires the flow velocity image of a cross section, which is within a flow path of the fluid to be imaged and is perpendicular to a cylindrical axis of the two-dimensional selective excitation region, and the flow velocity determination section determines, as the flow velocity of the fluid to be imaged, a maximum flow velocity on a profile of the flow velocity image in a flow path direction of the fluid to be imaged.

5. The magnetic resonance imaging apparatus according to claim 4, wherein the fluid to be imaged is blood, the flow velocity image acquisition section acquires the flow velocity image at multiple time phases covering one cardiac beat, and the flow velocity determination section interpolates the maximum flow velocity of each flow velocity image and determines the flow velocity as a function of time.

6. The magnetic resonance imaging apparatus according to claim 1, wherein the k-space ordering determination section determines a segment, in which an echo signal with a greatest effect of a pre-pulse is acquired, by dividing a distance between an application position of the two-dimensional selective excitation pulse and an imaging position by the velocity determined by the velocity determination section and the measurement time per segment.

7. The magnetic resonance imaging apparatus according to claim 2, wherein an RF pulse used as the two-dimensional selective excitation pulse is an IR pulse, the imaging parameter determination unit further includes a flip angle determination section that determines a flip angle of the IR pulse, and the flip angle determination section calculates the flip angle such that a time taken for the fluid to be imaged to travel by a distance between an application position of the IR pulse and an imaging position becomes an inversion time of the IR pulse using the velocity of the fluid to be imaged.

8. The magnetic resonance imaging apparatus according to claim 7, wherein the imaging parameter determination unit further includes a distance calculation section that, when the flip angle determination section is not able to calculate the flip angle, calculates the distance between the application position of the IR pulse and the imaging position from which the flip angle can be calculated and presents the calculated distance to an operator.

9. A fluid imaging method of acquiring an image of a fluid by dividing k space into a plurality of segments, applying a two-dimensional selective excitation pulse as a pre-pulse, and measuring echo signals of one or more segments each time the two-dimensional selective excitation pulse is applied using a magnetic resonance imaging apparatus, the method comprising:

an imaging parameter determination step of determining a velocity of a fluid to be imaged, and determining the number of segment execution times, which is the number of segments, amongst the plurality of segments of k space, measured each time the two-dimensional selective excitation pulse is applied, from the velocity of the fluid to be imaged, a size of an excitation region of the input two-dimensional selective excitation pulse, and measurement time per segment;

a k-space ordering determination step of determining an echo signal acquired in each segment such that an echo signal with a greater effect of the two-dimensional selective excitation pulse is arranged in a region closer to the center of k space, including determining a segment, in which an echo signal with a greatest effect of the two-dimensional selective excitation pulse is acquired, from the velocity of the fluid to be imaged and the measurement time per segment and arranges the echo signal near the center of k space;

a measurement step of measuring echo signals of each segment by the number of segment execution times and arranging the acquired echo signals in k space each time the two-dimensional selective excitation pulse is applied; and an image reconstruction step of reconstructing an image from the echo signals arranged in k space.

10. The fluid imaging method according to claim 9, further comprising:

a positioning image acquisition step of acquiring a positioning image before the imaging parameter determination step, wherein the imaging parameter determination step includes a parameter receiving step of receiving inputs of the measurement time per segment and the size of the excitation region of the two-dimensional selective excitation pulse on the positioning image, a velocity determination step of calculating the velocity of the fluid to be imaged, and a number-of-execution-times determination step of determining the maximum number of segments, among the numbers of segments to which the two-dimensional selective excitation pulse is applied at least once while the fluid to be imaged passes through the excitation region of the two-dimensional selective excitation pulse, as the number of segment execution times from the velocity of the fluid to be imaged, the size of the excitation region of the two-dimensional selective excitation pulse, and the measurement time per segment.

11. A magnetic resonance imaging apparatus that acquires an image of a fluid by dividing k space into a plurality of segments, applying a two-dimensional selective excitation pulse as a pre-pulse, and measuring echo signals of one or more segments each time the two-dimensional selective excitation pulse is applied, the apparatus comprising:

an imaging parameter determination unit that determines the number of segment execution times, which is the number of segments measured each time the two-dimensional selective excitation pulse is applied, from a velocity of a fluid to be imaged, a size of an excitation region of the input two-dimensional selective excitation pulse, and measurement time per segment, wherein the imaging parameter determination unit includes a velocity determination section that determines a velocity of the fluid to be imaged, and a k-space ordering determination section that determines an echo signal acquired in each segment such that an echo signal with a greater effect of the two-dimensional selective excitation pulse is arranged in a region closer to the center of k space, and wherein the k-space ordering determination section determines a segment, in which an echo signal with a greatest effect of the two-dimensional selective excitation pulse is acquired, from the velocity of the fluid to be imaged and the measurement time per segment and arranges the echo signal near the center of k space.

* * * * *